(12) United States Patent
Bianchi et al.

(10) Patent No.: US 8,058,239 B2
(45) Date of Patent: Nov. 15, 2011

(54) HMGB1 PROTEIN INHIBITORSAND/OR ANTAGONISTS FOR THE TREATMENT OF VASCULAR DISEASES

(75) Inventors: Marco E. Bianchi, Peschiera Borromeo (IT); Tiziana Bonaldi, Crema (IT); Paola Scaffidi, Cornaredo (IT); Susanne Mueller, Monza (IT); Bernard Degryse, Rognac (FR)

(73) Assignee: Bio3 Research S.r.l., Milan (IT)

( * ) Notice: Subject to any disclaimer, the term of this patent is extended or adjusted under 35 U.S.C. 154(b) by 35 days.

(21) Appl. No.: 11/968,506

(22) Filed: Jan. 2, 2008

(65) Prior Publication Data

US 2008/0171052 A1 Jul. 17, 2008

Related U.S. Application Data

(62) Division of application No. 10/471,641, filed on Feb. 17, 2004.

(30) Foreign Application Priority Data

Mar. 16, 2001 (IT) .............................. MI2001A0562

(51) Int. Cl.
*A61K 38/18* (2006.01)
(52) U.S. Cl. .......................................... 514/9.4; 514/7.9
(58) Field of Classification Search ........................ None
See application file for complete search history.

(56) References Cited

U.S. PATENT DOCUMENTS 6,054,122 A * 4/2000 MacPhee et al. ............ 424/94.4

FOREIGN PATENT DOCUMENTS

| WO | WO 9726913 | 7/1997 |
|---|---|---|
| WO | WO 9739121 | 10/1997 |
| WO | WO 9739125 | 10/1997 |
| WO | WO9822138 | 5/1998 |
| WO | WO0047104 | 8/2000 |
| WO | WO0076573 | 12/2000 |
| WO | WO 2006008779 A1 * | 1/2006 |

OTHER PUBLICATIONS

Parkkinen et al., J Biol Chem. Sep. 15, 1993;268(26):19726-38.*
Rauvala et al., Matrix Biol. Sep. 2000;19(5):377-87.*
Pins et al., J Invest Dermatol. Apr. 2000;114(4):647-53.*
Bear et al., Cell, vol. 101, 717-728, Jun. 23, 2000.*
Fawcett et al., The Journal of Cell Biology, vol. 128, 1995, pp. 1229-1241.*
Wells, 1990, Biochemistry 29:8509-8517.*
Ngo et al., 1994, The Protein Folding Problem and Tertiary Structure Prediction, pp. 492-495.*
Bork, 2000, Genome Research 10:398-400.*
Skolnick et al., 2000, Trends in Biotech. 18(1):34-39, especially p. 36 at Box 2.*
Doerks et al., 1998, Trends in Genetics 14:248-250.*
Smith et al., 1997, Nature Biotechnology 15:1222-1223.*
Brenner, 1999, Trends in Genetics 15:132-133.*
Bork et al., 1996, Trends in Genetics 12:425-427.*
Andersson et al., 2000 J. Exp. Med., vol. 192 565-70.
Chen et al., 2004. J Interferon and Cylokine Res. vol. 24: 329-33.
Degryse, B et al. The High Mobility Group HMG Boxes of the Nuclear Protein HMG1 Induce Chemotaxis and Cytoskeleton Reorganization in Rat Smooth Muscle Cells. J Cell Biol. 152, 1197-1206 (2001).
Hertel L et al. Decreased Expression of the High Mobility Group Protein T160 by Antisense RNA Impairs the Grwoth of Mouse Fibroblasts. Biochimie 79, 717-723 (1997).
Ronfani L et al Reduced Fertility and Spermatogenesis Defedts in Mice Lacking Chromosomal Protein HMGB2 Development 128, 1265-1273 (2001).
Stros M et al., A Role of Basic Residues and the Putative Intercalating Phenylalanine of the HMG1 Box B in DNA Supoercoiling and Binding to Four Way DNA Junctions. J Biol Chem 275(46), 35699-35707 (2000).
Yamazaki, F et al Repression of Cell Cycle Progression by Antigsense HMG2 RNA, Biochem. Biophys. Res. Comm 210(2), 1045-1051(1995).
PCT/IT02/00153, Intr Search Rpt.

* cited by examiner

*Primary Examiner* — Zachary Skelding
(74) *Attorney, Agent, or Firm* — Young & Thompson (57) ABSTRACT

The use of HMG box-binding molecules and molecules having sequence homology with HMG box for the preparation of therapeutic agents for the treatment of vascular diseases is described.

3 Claims, 10 Drawing Sheets

HMGB1 PROTEIN INHIBITORS AND/OR ANTAGONISTS FOR THE TREATMENT OF VASCULAR DISEASES

BACKGROUND OF THE INVENTION

1. Field Of The Invention

The present invention concerns the field of molecular biology and more particularly HMGB1 protein inhibitors and HMGB1 antagonists to be used for the treatment of vascular diseases, including those due to angioplasty.

2. Description Of The Related Art

HMGB1 protein(known, before 2001, as HMG; Bustin, 2001, Trends Biochem. Sci., 26, 152-153) is the archetypal protein of the HMG-box family, which is characterised by the presence of DNA binding domains, called HMG boxes. HMG1 is a small 25-kD protein, of 215 amino acids, with a highly conserved sequence among mammals. The HMGB1 molecule is organised into three domains: two DNA binding domains, HMG Box A and BoxB, which are followed by an acidic COOH terminus composed of 30 glutamic and aspartic residues. The two HMG boxes, box A and boxB, are 80 amino acid segments(29% identical, 65% similar), having an L-shaped tridimensional structure (Hardman et al., 1995, Biochemistry, 34 :16596-16607 Read et al., 1993, Nucleic Acids Res., 21: 3427-3436; Weir et al., 1993, EMBO J., 12: 1311-1319).

HMGB1 has originally been identified as a ubiquitously expressed, abundant nuclear protein. It is present in more than 1 million copies per single nucleus and binds double stranded DNA without sequence specificity.

Instead, HMGB1 binds with high affinity to specific DNA structures like kinked or bent DNA and four-way junctions. However, HMGB1 can be recruited to double stranded DNA by interaction with several different DNA binding proteins. When bound to double stranded DNA, it induces structure distortion, allowing the formation of nucleoprotein complexes where several DNA-binding proteins can contact each other while bound to their respective DNA cognate sites (Muller et al., 2001, EMBO J., 16: 4337-4340 and other reference cited herewithin). The phenotype of HMGB1-/- mice is in agreement with this mode I(Calogero et al., 1999, Nat. Genet., 22: 276-280).

Recently, an additional role for HMGB1 outside the cell nucleus has come into focus: HMGB1 works as late mediator of endotoxin-induced lethality as well as acute lung inflammation in mice; as well the elevated serum level of HMGB1 in septic patients is a prognosis marker (international patent application No. WO 00/47104). HMGB1 can be secreted by macrophages and pituicytes in culture in response to cytokines and bacterial endotoxin (Abraham et al., 2000, J. Immunol., 165:2950-2954; Wang et al., 1999, Surgery (St. Luis), 126 :389-392; Wang et al., 1999, Science, 285 : 248-251).

The release of HMGB1 from murine erythroleukemia cells is correlated with cell differentiation and the protein can be found in a plasma membrane-associated form in these cells (Passalacqua et al., 1997, FEBS Lett., 400 : 275-279; Sparatore et al. 1996, Biochem. J., 320: 253-256). A protein called amphoterin, identical in sequence to HMGB1, has been described in the brain, where it is found in the nucleus and cytoplasm of neuronal cells as well as in the extracellular space.

If exogenously added, HMGB1 mediates outgrowth of neurites, and laminin-dependent migration of neuroblastoma and glioma cells is inhibited by antibodies against HMGB1 (Fages et al., 2000, J. Cell Sci., 113: 611-620; Merenmies et al., 1991, J. Biol. Chem., 266 : 16722-16729; Parkkinen et al., 1993, J. Biol. Chem., 268: 19726: 19738; Rauvala et al., 1988, J. Cell Biol., 107: 2293-2305). Interactions between HMGB1 and the plasminogen activation system, in particular t-PA (tissue-type plasminogen activator), results in enhanced plasmin formation (Parkkinen and Rauvala, 1991, J. Biol. Chem., 266: 16730-16735). Degradation of extracellular matrix proteins is an important step in the cell migration process, and HMGB1-promoted increase of extracellular protease activity might enable the cells to migrate.

HMGB1 has been identified as one of the ligands binding to the RAGE receptor (Receptor for advanced glycation end-products)(Hori et al., 1995, J. Biol. Chem., 270:25752-25761). RAGE is a multiligand receptor of the immunoglobulin super family and is expressed in many cell types, including endothelial cells, smooth muscle cells, mononuclear phagocytes, and neurons (Brett et al., 1993, Am. J. Phathol., 143 : 1699-1712; Neeper et al., 1992, J. Biol. Chem., 267: 14998-15004). It is implicated in several different pathological processes, such as diabetes, amyloidoses, and atherosclerosis (Schmidt et al., 1999, Circ. Res., 84: 489-497). Interaction of HMGB1 and RAGE induces neurite outgrowth, and the two proteins colocalize at the leading edge of advancing neurites during embryonic development (Huttunen et al., 1999, J. Biol. Chem., 274:19919-19924). The block of tumour growth and metastasis is observed preventing the interactions between HMGB1 and RAGE; moreover, inhibition of this interaction suppresses activation of mitogen-activated protein (MAP) kinases and the expression of matrix metalloproteinases, molecules importantly linked to tumour proliferation and invasion (Taguchi et al., 2000, Nature, 405: 354-360).

The inventors of the present invention, demonstrated that HMGB1 has a potent biological effect on smooth muscle cells (SMC), one of the cell types where RAGE is expressed on the surface. Vascular SMC cells are the most predominant cells of the larger blood vessels; they are located in the tunica media where are embedded in the extracellular matrix. In intact vessels, SMC cells are in a contractile state and show a phenotype characterised by the absence of cell division and migration responsible for vessel wall rigidity and elasticity maintenance and blood pressure control.

When the endothelium is damaged, either after mechanical or inflammatory injuries, SMC cells switch to a synthetic phenotype and undergo cell division and cell migration. The migration of SMC cells from the tunica media to the tunica intima, resulting in intimal thickening, plays an important role in the pathophysiology of many vascular disorders, such as atherosclerosis and restenosis after coronary angioplasty. In the synthetic state, SMC cells also produce higher amounts of extracellular proteinases, growth factors, and cytokines and secrete a fibrous extracellular matrix. After vessel wall injury, the release of several growth factors and/or chemoattractants either by circulating monocytes, macrophages and platelets, or by damaged endothelial cells can induce SMC cells switch from the contractile to the synthetic phenotypes and it can direct the migration of SMC cells towards the vessel intima. Among these factors, bFGF appears to be one of the most important, but however, SMC cells can also start migration in response to angiogenic stimuli (Schwartz, 1997, J. Clin. Invest., 99: 2814-2816; Van Leeuwen, 1996, Fibrinolysis, 10:59-74).

SUMMARY OF THE INVENTION

Trying to define the effect and the mechanism by which HMGB1 induces RSMC cell migration, the inventors demonstrated that HMGB1 is a strong chemoattractant and it induces their cell shape changes, and cytoskeleton reorganisation. These events are inhibited by addition of an anti-RAGE antibody and by pertussis toxin, i underlining that both RAGE and aGi/o protein might be involved in the pathway. Furthermore, the evidence that HMGB1 promotes the translocation of phosphorylated ERK 1 and 2 proteins into the nucleus, indicates the involvement of the MAP kinase pathway. Then, it has been demonstrated that HMGB1 is released by damage or necrosis of a variety of cell types, including endothelial cells. Therefore, HMGB1 has all the hallmarks of a molecule that can promote atherosclerosis and restenosis after vascular damage.

The inventors also demonstrated that HMGB1 fragments, corresponding to HMG boxes, are more efficacious than the entire full-length molecule and even HMG box domains of other proteins of the HMG-box family can induce the same effects.

Consequently, every kind of molecules able to block the interaction between HMGB1 and its RAGE receptor (i. e. all the molecules belonging to the inhibitors class: antibodies or antibodies fragments, fourway DNA; and all the molecules belonging to the HMG box antagonist class: HMGB1 fragments molecules containing the HMG box domain) can efficiently be used for the production of pharmacological preparation in order to avoid, retard or inhibit atherosclerosis and restenosis after vascular epithelium damage even due to angioplasty.

HMGB1-binding molecules or HMGB1 inhibitors can be injected or released by instruments used for angioplastic surgery, or said molecules can be bound to the instruments' surface.

Object of the present invention is the use of molecules able to block the interaction between HMGB1 and RAGE for the preparation of therapeutic agents for the treatment of vascular diseases.

In a preferred embodiment of the invention said molecules are released by catheters, surgical instruments or stents for angioplasty, during or after said operation.

BRIEF DESCRIPTION OF THE DRAWING FIGURES

Further features and advantages of the invention will be more readily apparent from the following detailed description with reference to the accompanying drawings. In the drawings:

FIG. 1-A shows concentration-dependent migratory response of RSMC to HMGB1 purified from calf thymus. FIG. 1-B shows the comparison of the chemotactic effect of HMGB1 proteins, either purified from calf thymus or expressed in yeast, with those of chemoattractants fMLP and bFGF. FIG. 1-C shows the effect of anti-HMGB1 antibodies on fMLP—and HMGB1—induced migration. The asterisk (*) indicates treatments where the migratory response was statistically different from the control beyond the p=0.0001 limit in Student's test. FIG. 1-D shows the concentration-dependent migratory response of RSMC to HMGB1 expressed in yeast (*Pichia pastoris*). FIG. 2-A shows the effect of HMGB1 purified from calf thymus or expressed in yeast or in *E. coli* on subconfluent cultures of RSMC. Actin filaments were visualised using TRIC-phalloidin. FIG. 2-B shows how anti-HMGB1 rabbit antibodies inhibit HMGB1-stimulated cytoskeleton reorganization. Resting cells (state 1) exhibit numerous stress fibers. Non-resting cells (state 2) show a reorganization of actin cytoskeleton.

FIG. 3-A shows the concentration-dependent response to Box A e Box B, both expressed in *E. coli*. Random cell migration is referred to as 100% migration. The data represent the mean+SD (n=3). The statistical significance of the result is p<0.0001 in a ANOVA model, for both Box A and Box B.

FIG. 3-B shows the effects of full-length HMGB1 expressed in *E. coli*, Box A+B, Box A or Box B on actin cytoskeleton organization. Actin filaments were visualized using TRIC-phalloidin.

FIG. 5-A shows that large amounts of HMGB1 bind to the surface of RSMC. In FIG. 5-B RSMC expressing RAGE are shown. FIG. 5-C shows how anti-RAGE antibody inhibits HMGB1-induced RSMC migration. Statistical significance is $0.001<p<0.0001$ for treatment with HMGB1 and HMGB1 plus unspecific antibody.

In FIG. 6-A chemotaxis assays performed using modified Boyden chambers are shown. The value of 100% corresponds to basal cell migration in the absence of any stimulator; the data represent the mean+SD. FIG. 6-B shows evident cytoskeleton reorganization, actin filaments were visualised using conjugated TRITC-phalloidin.

FIG. 8-A shows the results of Western-blot analysis of proteins released by necrotic, or permeabilized HeLa; HMGB1 presence is evident in line 1 and line 3. FIG. 8-B shows the results of immunofluorescence assays performed on necrotic and living HeLa.

In FIG. 9-A and in FIG. 9-B it is shown that HMGB1 is present in the nuclei of endothelial cells but it is not detectable in the nuclei of vascular smooth muscle cell of a section of human pancreatic artery stained with anti-HMGB1 antibody and counterstained with ematoxylin, at low (A) and high (B) magnification. The red frames indicate the location of the area shown in FIG. B and the arrows point to the nuclei of SMC. In FIG. 9-C Western blot analysis shows expression level of HMGB1 in RSMC in comparison to HeLa cells.

DETAILED DESCRIPTION OF THE INVENTION

Expression and Purification of HMGB1 and Derivates

In the first step, it has been necessary to express and purify HMGB1 and derivates. Expression of full-length HMGB1 was performed in *E. coli* transformed with pT7-7-rHMG1cm plasmid (kind gift of Prof. J. O. Thomas, Cambridge University) and purification was performed following a well-know protocol (Muller et al., 2001, Biochemistry, 40: 10254 0261).

Expression and purification of full-length HMGB1 in yeast Pichia Pastoris were performed following a well known protocol (Mistry et al., 1997, Biotechniques, 22: 718-729).

The well-known plasmids pRNHMG1/M1-V176, pT7Hegira and pT7HMGlbB were used for the expression and purification of Box A+Box B, Box A and Box B respectively following well-know procedures of purification of the single and double boxes (Bianchi et al., 1992, EMBO J., 11 : 1055-1063).

To demonstrate chemotactic effect of HMGB1, three independent cell migration assays were performed : chemotaxis assay, chemokinesis assay and in vitro wounding assay. The functional relationship between HMGB1-induced cell migration and morphological changes (i. e. actin fibers reorganization, cell elongation and cell's shape polarization) of non resting cells was investigated.

Chemotaxis Assay

Chemotaxis assays were performed using well-known protocols (Degryse et al., 1999, Blood, 94: 649-662).

Modified Boyden chambers were used with filters having 0.5 Am pore size (Corning, Acton, Mass.) and treated with collagenI (100 Ug/ml in 0.5 M acetic acid) e fibronectin (10 llg/ml) (Roche). RSMC cells (kind gift of Dr. Marco Bertulli, Bayer Research Laboratories, Milan) were cultured in DMEM serum-free and a sample of 20,000-40,000 cells was added to the upper well of Boyden chamber. The molecules to be tested were diluted in the same serum-free medium and added to the lower well.

Different HMGB1 preparations were used: HMGB1 purified from calf thymus (kind gift of J. Bernues, C.S.I.C., Barcelona, Spain), *E. coli* expressed recomb anti-HMGB1, and a lightly modified HMGB1 form (containing EAEAYVEF aminoacids bound to the N terminus) produced in yeast *Pichia pastoris* (Mistry et al., 1997, Biotechniques, 22: 718-729).

If necessary, the polyclonal rabbit anti-HMGB1 (Pharmingen B D, Torrey Pines, Calif.), the pertussis toxin (PT) from *Bordetella pertussis* (kind gift of Dr. M. G. Pizza, I. R. I. S., Siena) or the inhibitors were added in both wells.

Overnight cell migration was allowed at 37 C, then cells remaining on the upper surface of filters were scraped off and filters were fixed in methanol and stained in a solution of 10% crystal violet in 20% methanol. All experiments were performed at least twice in triplicate.

Figure 1:
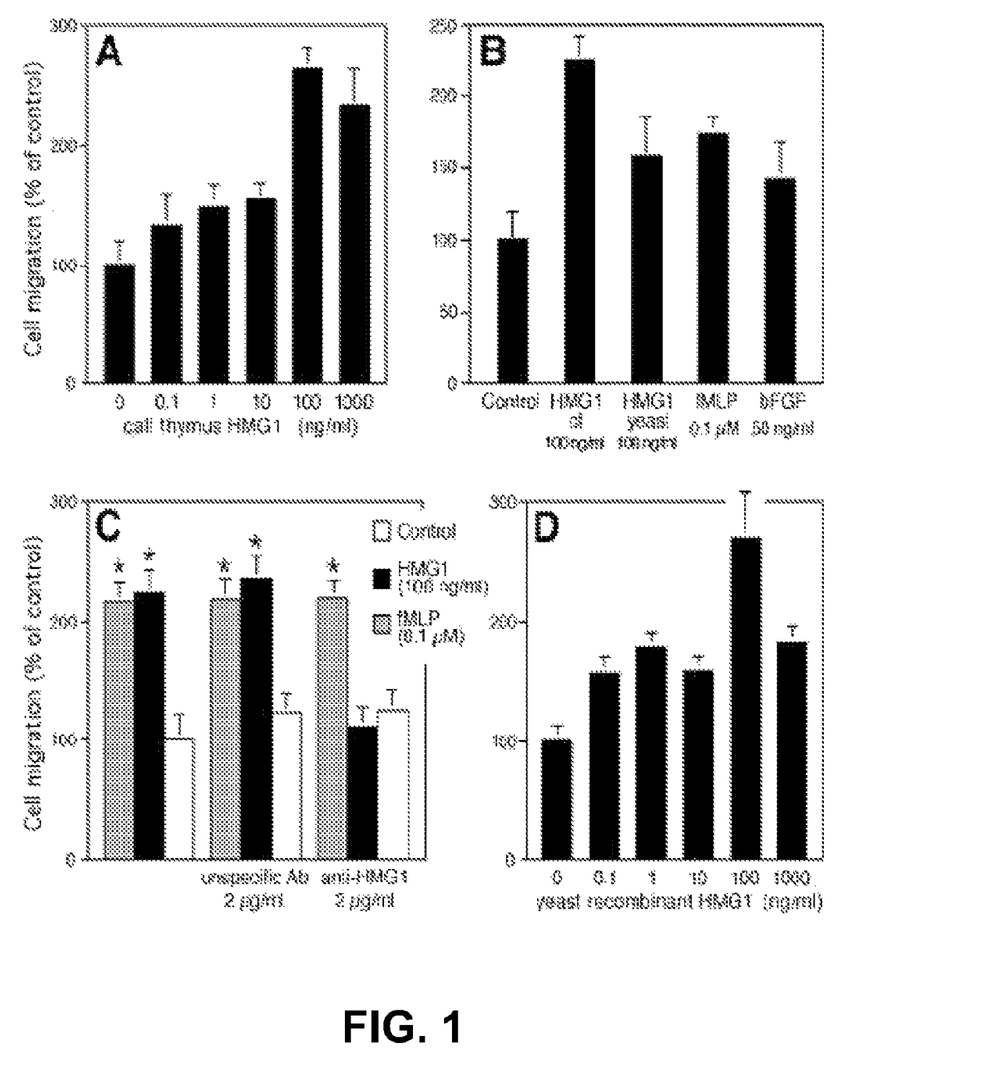
FIG. 1 shows HMGB1 chemotactic activity on RSMC in chemotaxis assays performed using modified Boyden chambers. The value of 100% corresponds to the number of cells migrating in the absence of any stimulator (random cell migration). The data represent the mean+SD (n=3).

Results, as shown in FIG. 1-A, 1-B, 1-C, 1-D, are the mean+SD of the number of cells counted in 10 high power fields per filter and expressed as fold over control. To random cell migration (i. e., migration in the absence of chemoattractant) was given the arbitrary value of 100%.

Statistical analysis was performed using Student's t test for pairwise comparisons of treatments, or an ANOVA model for the evaluation of treatments with increasing doses of a reagent.

HMGB1 from calf thymus stimulates migration of RSMC in a concentration-dependent manner, starting at doses as low as 0.1 ng/ml and with a 2.5-fold maximal response at 100 ng/ml (FIG. 1-A). The effect of HMGB1 is, comparable in amplitude to the effects of the well characterised attractants fMLP and bFGF (FIG. 1-B).

Polyclonal antibodies against I-IMGBS, but not: non specific control antibodies, totally block the migratory response (FIG. 1C), showing that this is specifically due to HMGB1. These antibodies fail to alter the effect of the chemoattractant peptide fMLP used as positive control. Similar results are obtained with recombinant HMGB1 produced in yeast *P. pastoris* (FIG. 1-D).

Immunofluorescence Assay

Samples of 15,000-20,000 RSMC, 20-40% confluence, 2 were seeded on glass coverslips in 2 cm wells and cultured for 24 hours in DMEM plus 10% FCS, washed with PBS, and cultured for another 24 hours in DMEM without FCS. RSMC were stimulated with HMGB1 100 ng/ml for increasing time intervals, from 5 to 120 minutes at 37 C. After stimulation, RSMC were fixed for 20 minutes at room temperature with a solution of 3% paraformaldehyde, 2% sucrose in PBS, pH 7.5, followed by three washes with PBS-BSA 0.2%. Cells were permeabilized with 20 mM Hepes pH 7.4, 300 mM saccharose, 50 mM NaCl, 3 mM MgCl2, 0.5% (v/v) Triton X-100 for 3 minutes at 4 C, and washed again three times with PBS-BSA 0.2%. Then, RSMC were incubated with PBS-BSA 2% for 15 minutes at 37 C, with primary antibodies for 30 minutes at 37 C, washed three times with PBS-BSA 0.2%, and further incubated with PBS-BSA 2% for 15 minutes. At the end, cells were stained with secondary antibodies and/or phalloidin conjugated with rodamin for visualization of filamentous actin; in some cases, DAPI (4',6-diamidino-2-phenilindolo, Roche) was used to label the nucleus.

After all the subsequent incubation, coverslips were washed three times with PBS-BSA 0.2%, twice with distilled water, mounted with 20% Mowiol in PBS and analysed on a Axiophot microscope (Carl Zeiss).

Fluorescence photographs were taken either on T-Max 400 or EPH P1600X film (Eastman Kodak) using Zeiss 40 and 100 neofluar lenses.

Figure 2:
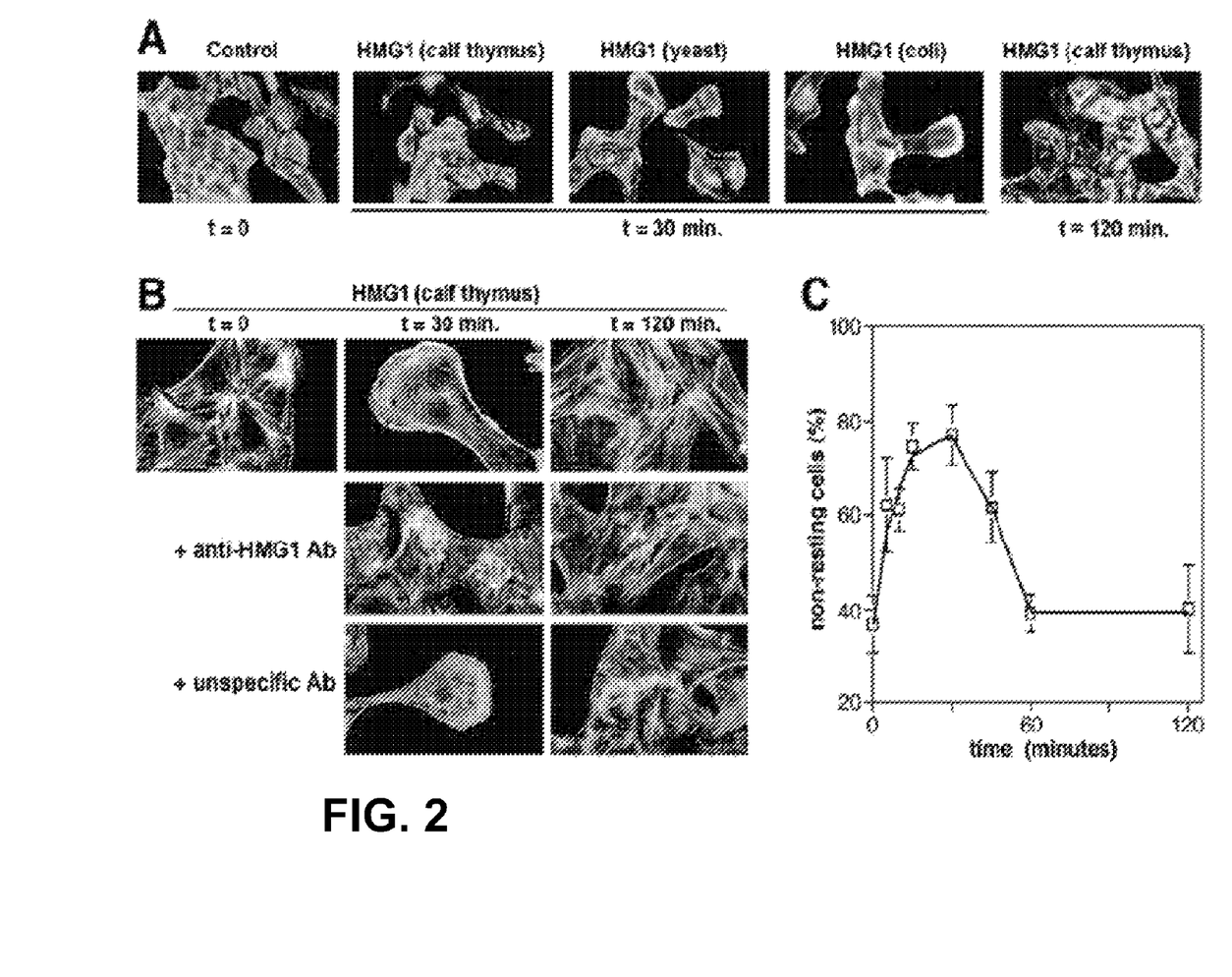
FIG. 2. shows the effect of HMGB1 on RSMC morphology and cytoskeleton organization.
Figure 3:
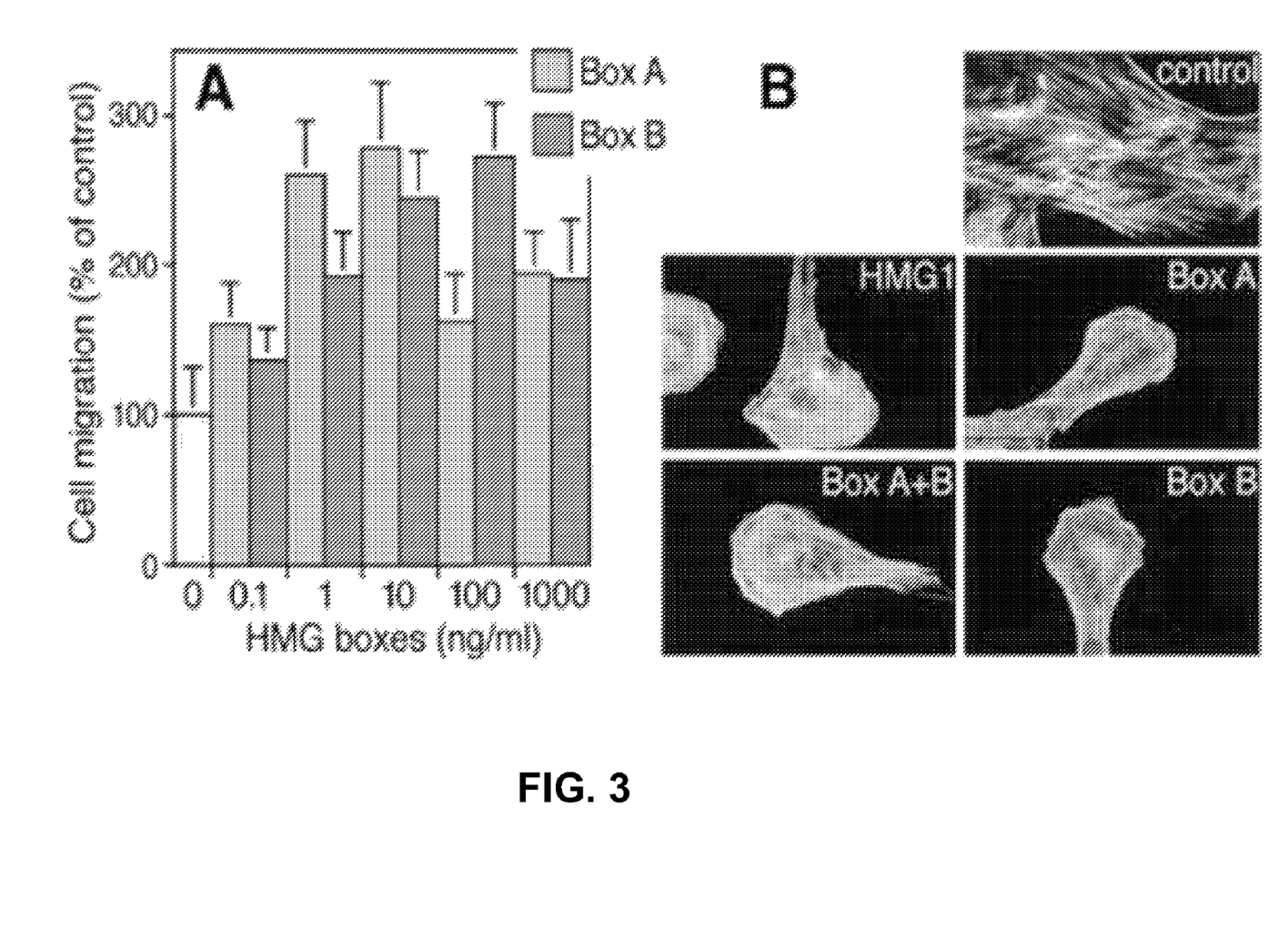
FIG. 3 shows the chemotactic response of RSMC to the HMG box domains of HMGB1.

Low magnification pictures, in FIG. 2-A, show that stress fibers content, cell shape and size, and cytoskeleton organization change within 30 minutes, but reverse after 120 minutes. Higher magnification pictures (FIG. 2-B) show that before stimulation are well-visible numerous stress fibers and the cell shape is anonpolarized. Within 15-30 minutes, a complete change of morphology and cytoskeleton organization occurs: RSMC show an elongated, polarized morphology that reflected the spatial rearrangement of the actin cytoskeleton. The effects of HMGB1 slowly decrease : After 1-2 hours, the stress fiber content increases back to the initial level and cell morphology returns similar to that of unstimulated control cells.

In certain experiments cells were overnight pretreated with antibodies or PT or inhibitors. As shown in FIG. 2-B, antibodies against HMGB1 totally inhibit the cytoskeletal reorganization and the morphological change of RSMC induced by HMGB1. Control antibodies are not able to inhibit HMG1 effects.

Finally, to determine whether the observed effects of HMGB1 on RSMC actually reflect a dynamic transition from resting to motile states, the proportion of cells in each different state was quantified. Low magnification pictures were taken and the cells were classified in two states:

state 1, where cells show the appearance typical of unstimulated cells characterized by a high number of stress fibers and a non polarized cell shape;

state 2, where RSMC exhibiting a low stress fibers content, membrane ruffling, actin semi-rings, or an elongated shape.

It is clearly shown in FIG. 2-C that in unstimulated cultures 60% of the cells are in state 1 and 40% in state 2; within 5 minutes after stimulation the proportion of cells in state 2 increases to 60%, and rose to 80% after 15-30 minutes. One hour after stimulation with HMGB1, these proportions reverse back to the values of unstimulated cultures, with 60% of RSMC in state 1 and 40% in state 2. These data demonstrate that HMGB1 effects are transient and represent the change from a resting to a migrating state, these data confirm chemotaxis results: HMGB1 is a chemoattractant for RSMC.

In Vitro Wounding Assay

Confluent cultures of RSMC, grown on glass coverslips in 2-cm2 wells, were washed once with PBS and FCS starved for 24 hours in serum-free DMEM. Then to simulate the wound, a single line was made with the tip of a pipette in the central region of the monolyaers.

The so treated monolayers, were washed once with PBS and are allowed to recover for 48 hours in serum-free medium supplemented or not with HMGB1 (100 ng/ml). Then cells were fixed and stained with TRITC-phalloidin.

Quantification of the migration was made by taking photographs at lower magnification and by counting the number of cells that had migrated into the cell-free space. The data represent the mean+SD and the value 100 t corresponds to the number of cells migrating in the absence of any stimulator (basal migration).

Figure 4:
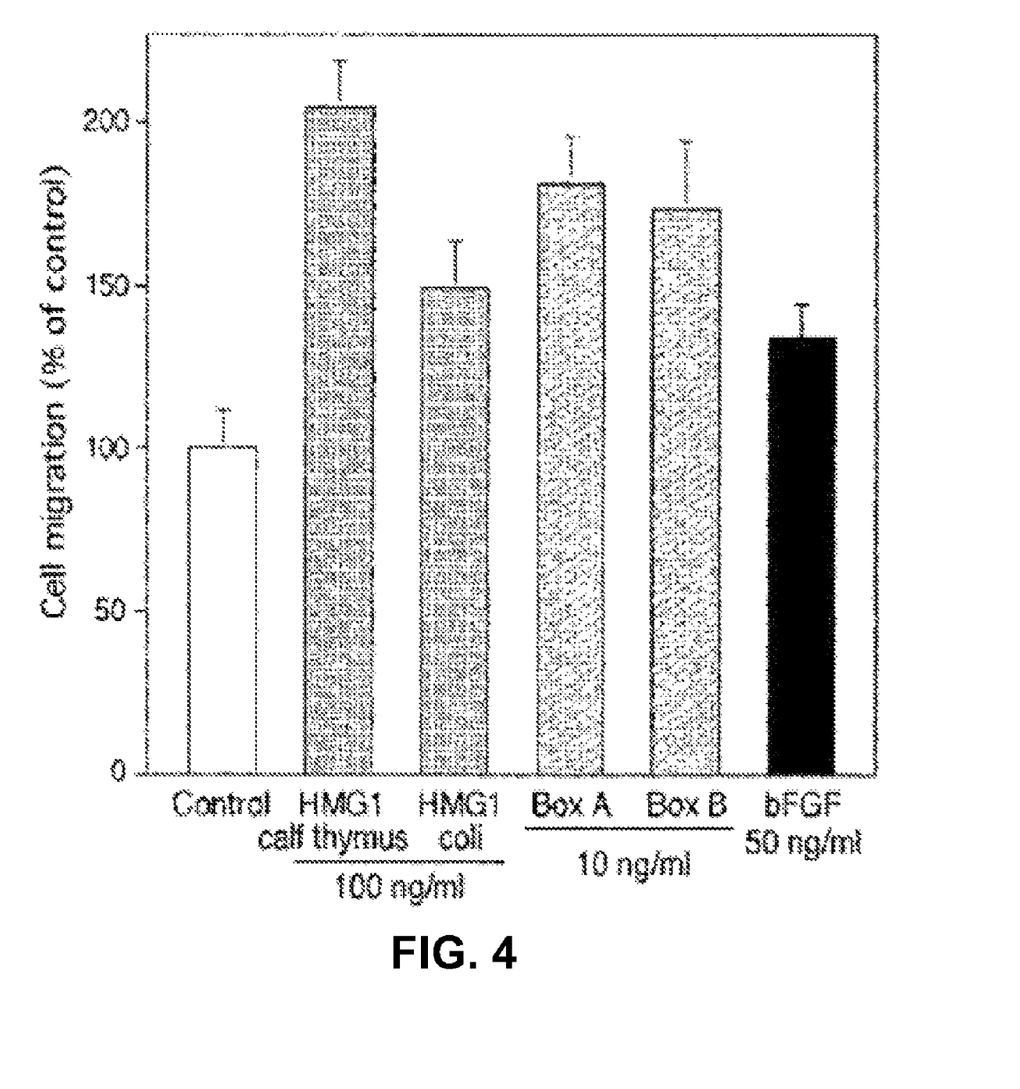
FIG. 4 shows the effects of HMGB1 and its HMG boxes on RSMC migration into a wound. The value of 100% corresponds to the number of cells migrating in the absence of any stimulator (basal migration). The data represent the mean-SD (n=5). Statistical significance is $0.05<p<0.01$ for the treatment with bFGF and full length bacteria-made HMGB1, $0.01<p<0.001$ for the treatment with Box A and Box B and $0.001<p<0.0001$ for the treatment with calf thymus HMGB1.

As shown in FIG. 4, HMGB1 stimulation increases the number of migrating cells by 5-2-fold. Box A and Box B (10 ng/ml) were also tested and both stimulate cell migration 1.8-fold. Finally, the comparison with bFGF (50 ng/ml) underlines that the above mentioned molecules are more effective. It is possible to assume that wound healing is based on the same signaling pathway of chemotaxis and chemokynesis.

Signaling Pathway

Afterwards, signaling pathway has been detected.

To act as a migratory signal, HMGB1 must arrive to the membrane of responsive cells and bind to a receptor. To test whether HMGB1 binds to the surface of RSMC, one million cells were trypsinized and incubated for 20 minutes at 4 C in PBS containing 800 ng of the Box A+B peptide and 5 pg BSA. The Box Al-Box B polypeptide is slightly smaller than the endogenous full-length HMGB1 and can thus be distinguished easily on SDS-PAGE gels. Then, cells were pelleted and the supernatant was saved after two washes in 500 pl cold PBS, cells were resuspended in SDS-PAGE sample buffer, heated for 5 minutes at 100 C and loaded on 12% tricine-SDS gel (line P), adjacent to 20 pl of supernatant (line S).

Figure 5:
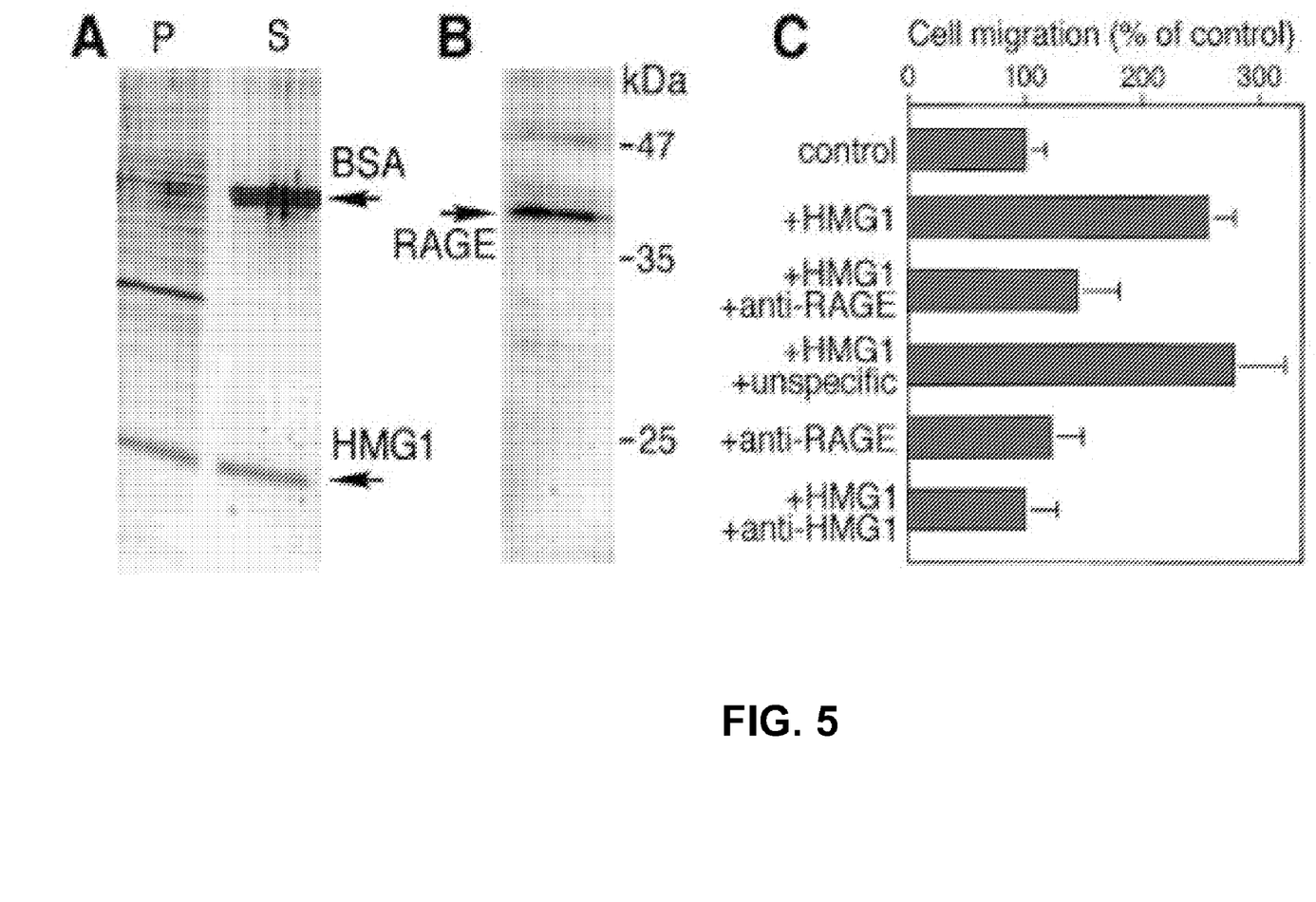
FIG. 5 shows how HMGB1 binds to the surface of RSMC and stimulates cell motility through RAGE.

Then, the gel was blotted to almmobilon filter, which was stained with India ink. In FIG. 5-A a SDS-PAGE gel is shown, from which the amount of Box A+B recovered in the cell pellet and in the supernatant can be calculated, and it can be estimated that more than 500,000 Box A+B molecules bind to a single RSMC. This result demonstrates that extracellular HMGB1 can bind to RSMC, but most likely does not reflect the actual receptor number. Indeed, HMGB1 has already been shown to bind to heparin and proteoglycans (Bianchi, 1988, EMBO J., 7: 843-849; Nair and Jungalwala, 1997, J. Neurochem., 68: 1286-1297; Saimivirta et al., 1992, Exp. Cell Res., 200 : 444-451); thus, HMGB1 might also be associated with the extracellular matrix produced by RSMC, as already demonstrated by the inventors in HeLa, where only small amounts of HMGB1 bind to cells because these cells produce little extracellular matrix.

HMGB1 has been reported to bind to RAGE that is expressed by a vast range of cell types. To demonstrate that RAGE is present on RSMC membrane, one million RSMC were lysed in a plate containing SDS-PAGE sample buffer (50 mM Tris pH 6.8, 2% 2-mercaptoethanol, 4% SDS, 12% glicerol, 0.05% bromophenol blue), denaturated for 5 minutes at 100 C and separated on 12% acrylamide. Separated proteins were blotted on Immobilon (Millipore) membrane using a tankblot system 25 mM Tris pH 7.5, 0.192 M glycine, 20% methanol. The blot was blocked for one hour at room temperature in 5% skim milk/TBST (20 mM Tris, pH 7.5, 137 mM NaCl, 0.1% Tween 20), three time washed in TBST, and incubated with anti-HMGB1 antibody in TBST-0.01% BSA. Incubation with secondary antibody was conducted after washing with TBST-0.01% BSA. Proteins were detected with ECL system (Amersham). The presence of RAGE was detected using anti-RAGE antibody (kind gift of Dr. A. M. Schmidt, Columbia University, N.Y.). Results shown in FIG. 5-B demonstrate that RAGE is present on RSMC. Furthermore, HMGB1-induced chemotaxis is not only inhibited by anti HMGB1 antibodies but also by anti-RAGE antibodies, as shown in FIG. 5-C. Anti-RAGE antibodies block cytoskeletal reorganization and morphological changes of RSMC in response to HMGB1 migratory signal; irrelevant antibodies are not able to block cytoskeleton reorganization. These data indicate that the RAGE receptor is required for the HMGB1-induced responses of RSMC.

Knowing that many chemoattractants act via membrane receptors associated to heterotrimeric GTP binding proteins (G proteins), whether G proteins could be implicated in HMGB1 signaling was tested. The pertussis toxin (PT) was used because it inhibits a specific subclass of G proteins, the Gi/o proteins, and it reveals their involvement in the signaling pathway (Baggiolini et al., 1994, Adv. Immunol., 55: 97-179; Haribabu et al., 1999, J. Biol. Chem., 274: 37007-37092). mPT, an inactive mutant of PT, was used as a control. RSMC were pre-treated with PT or with mPT (50 ng/ml) for 6 hours, thus stimulated with HMGB1 (100 ng/ml), Box A or Box B (10 ng/ml) for 30 minutes.

Figure 6:
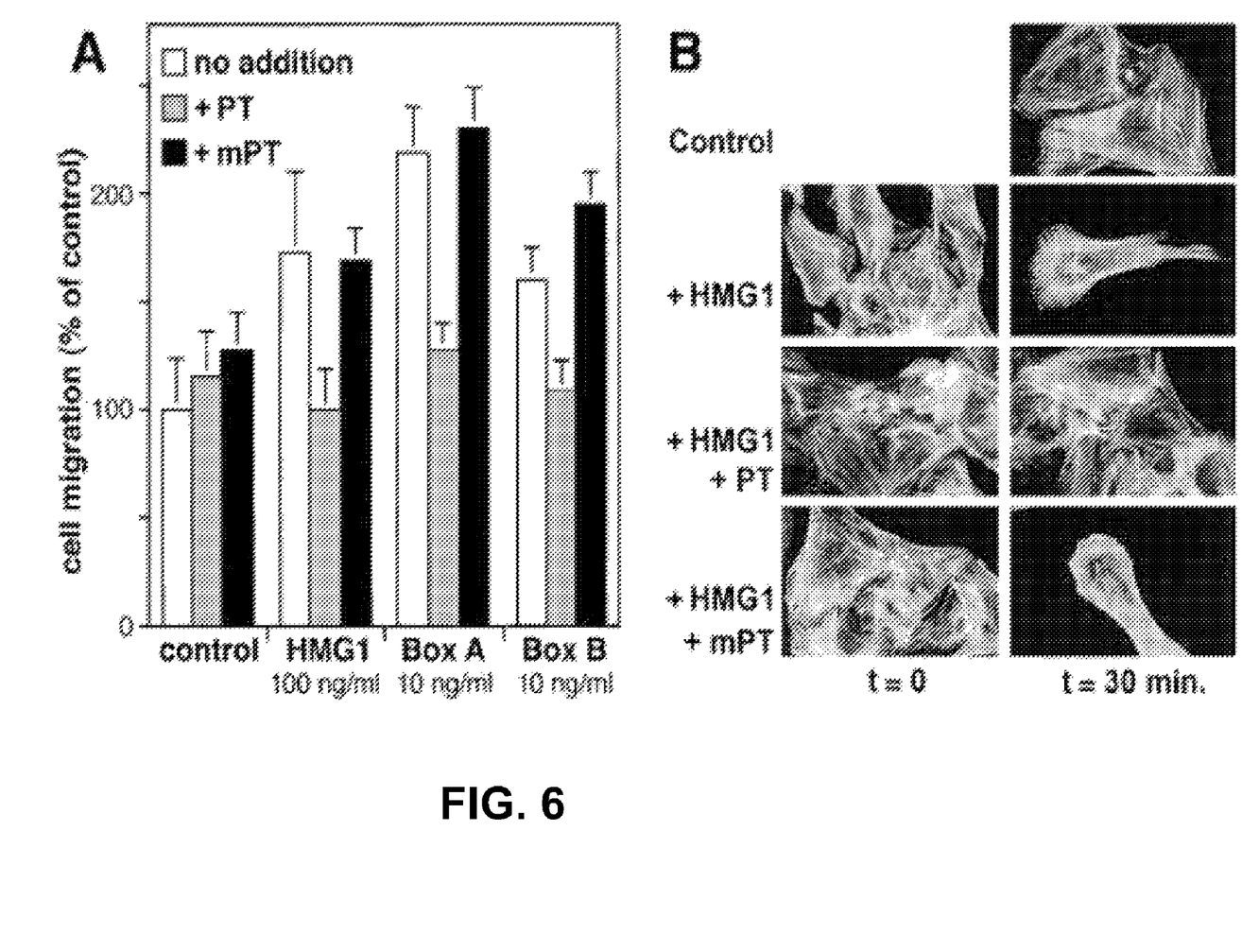
FIG. 6 shows how pertussis toxin (PT) inhibits HMGB1-induced RSMC migration and actin cytoskeleton reorganization.

Chemotaxis assays were performed as previously described. The data represent the mean+SD and the value of 100% corresponds to basal migration in the absence of any stimulator. In FIG. 6-A the inhibitory effect of PT on HMGB1-induced chemotaxis is shown.

These data suggest the involvement of Gi/o proteins in the signaling pathway controlled by HMGB1. In FIG. 6B the cytoskeleton reorganization is shown, actin filaments were visualised as previously described.

Figure 7:
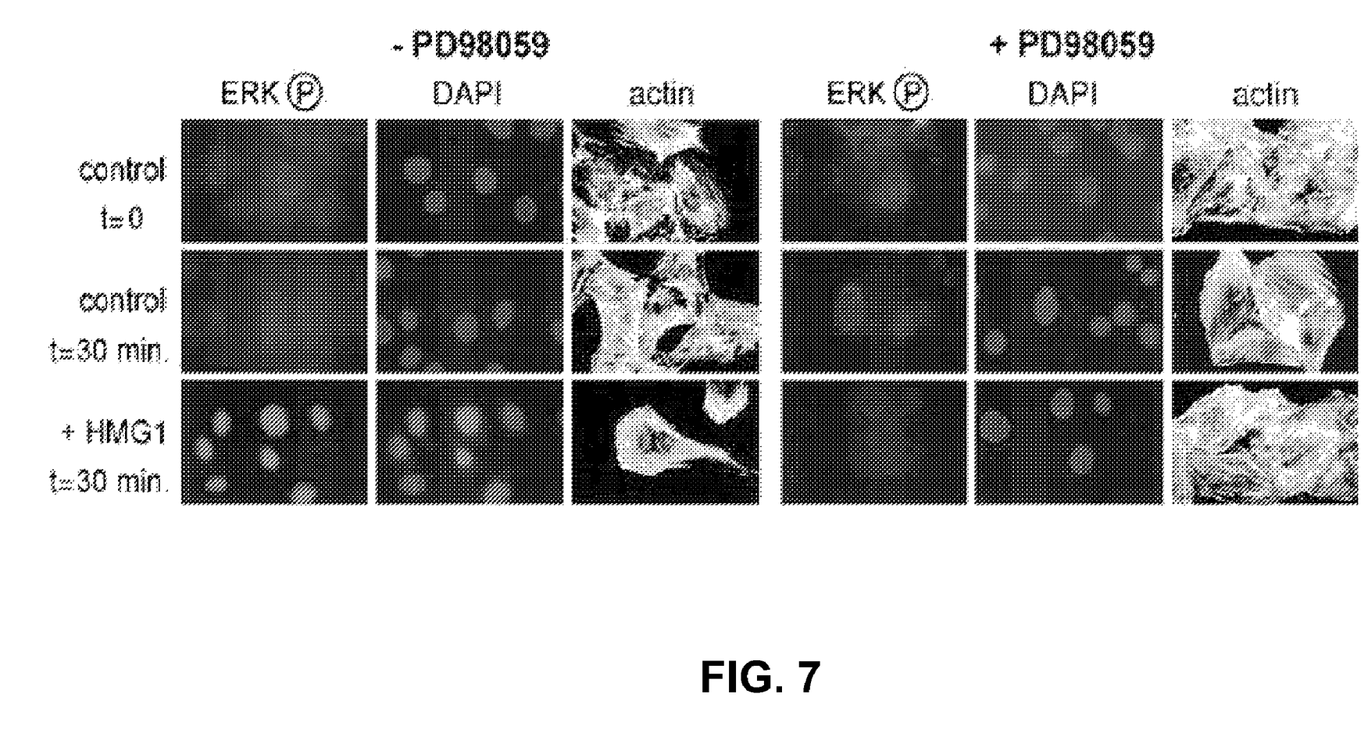
FIG. 7 demonstrates that the MAP kinase pathway is involved in HMGB1 signaling. Cells are stained with specific antibody against phosphorylated ERK1/2 and DAPI, and a separate sample of cells is stained with TRITC-phalloidin to visualize the reorganization of the cytoskeleton.

Afterwards, whether the HMGB1-induced signaling involves the MAP kinase pathway, was investigated; in fact, it is known that these proteins are activated by RAGE, and they have a direct role in the regulation of the intracellular motility machinery. RSMC were pretreated with PD98059 (50 mM) for one hour or were not pre-treated, stimulated for 30 minutes with HMGB1 from calf thymus (100 ng/ml) and stained with specific antibodies against phosphorylated ERK1/2 (New England Biolabs, Beverly, Mass.) and DAPI. A separate sample of cells was stained with TRITC-phalloidin to visualize the reorganization of cytoskeleton. In FIG. 7 is shown how, within 30 minutes, HMGB1 stimulation induces the activation of ERK1/2 proteins in RSMC and induces their nuclear translocation; in contrast, phosphorylated ERK proteins are hardly detectable and located in the cytoplasm, in unstimulated RSMC. Moreover, PD98059, the selective inhibitor of MEK, the upstream regulator of ERK, inhibits HMGB1-induced ERK phosphorylation and nuclear translocation, as well as RSMC migration and citoskeleton reorganization.

Consequently, these data show that the MAP kinase pathway plays an essential role in HMGB1-induced cell migration.

Induction of Cell Damage

Considering the state of the art, has been detected whether damaged cells or cells undergoing necrosis could release HMGB1 in the extracellular medium.

HeLa cells and HUVEC were induced to undergo necrosis by treatment with 5 UM ionomycin (Sigma) and 20 AM CCCP, or mM deoxyglucose and 10 mM sodium azide. After 16 hours at a 37 C, the number of cells undergoing necrosis was scored morphologically, and when it approached 50% the supernatant was collected.

For Western blot analysis, the medium from treated and untreated cells was collected and concentrated 50 fold using AmiconUltrafree-MC filters the cells were dissolved in the SDS-PAGE sample buffer.

For immunofluorescence analysis, the cells were fixed with 4% PFA, incubated with an anti-HMGB1 antibody, and stained with secondary antibody and DAPI. The permeabilization of cells was performed with using 0.1 tNP-40 in PBS.

Figure 8:
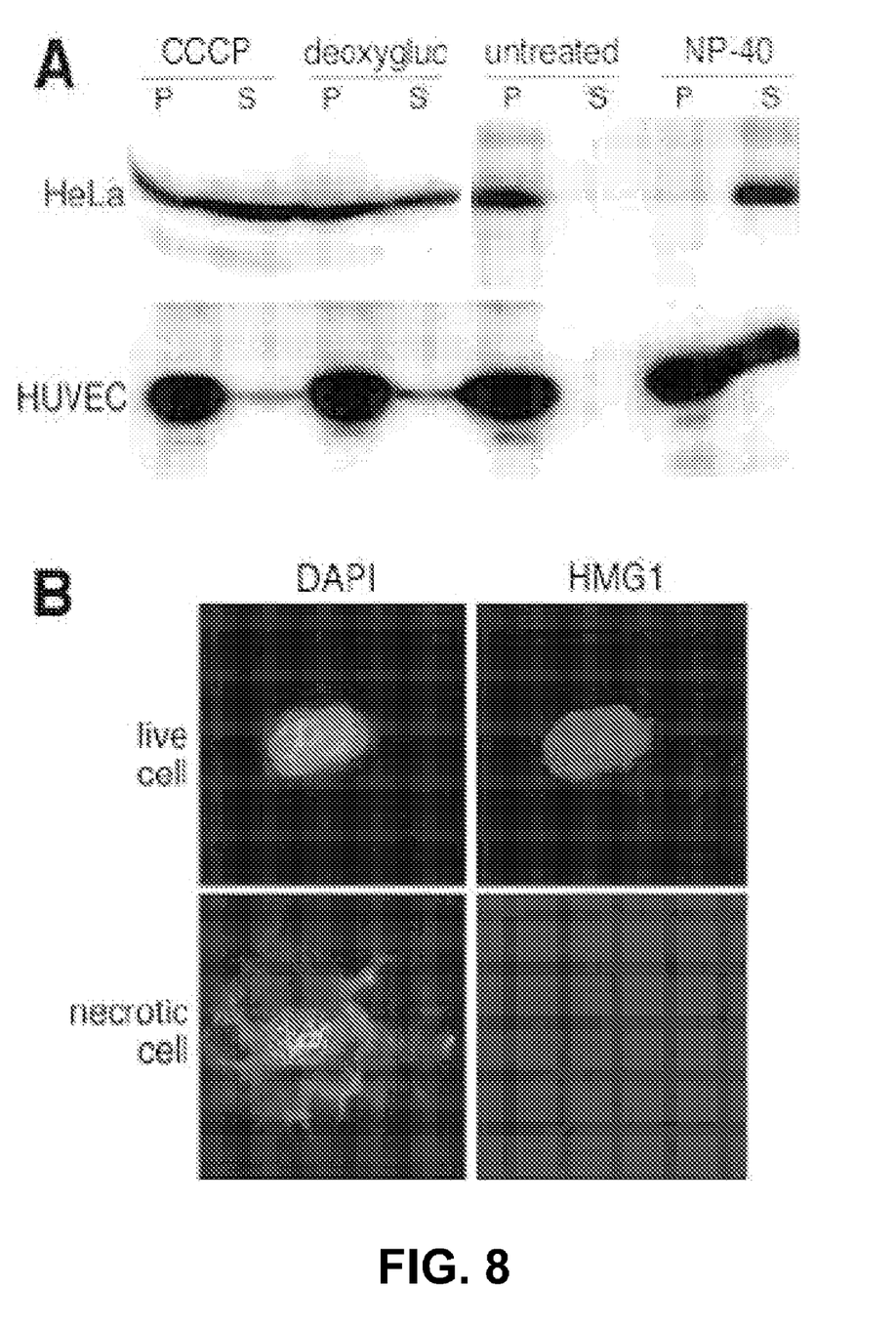
FIG. 8 shows that HMGB1 is released by necrotic and damaged cells.

In FIG. 8-A, Western-blot analysis of protein in supernatants (S) and cell pellets (P) is represented.

HMGB1 was recovered in the supernatant of both necrotic cells and damaged cells. In FIG. 8-B immunofluorescence assays performed on single living and necrotic HeLa is shown, HMGB1 is not associated to the remnants of necrotic cells.

Figure 9:
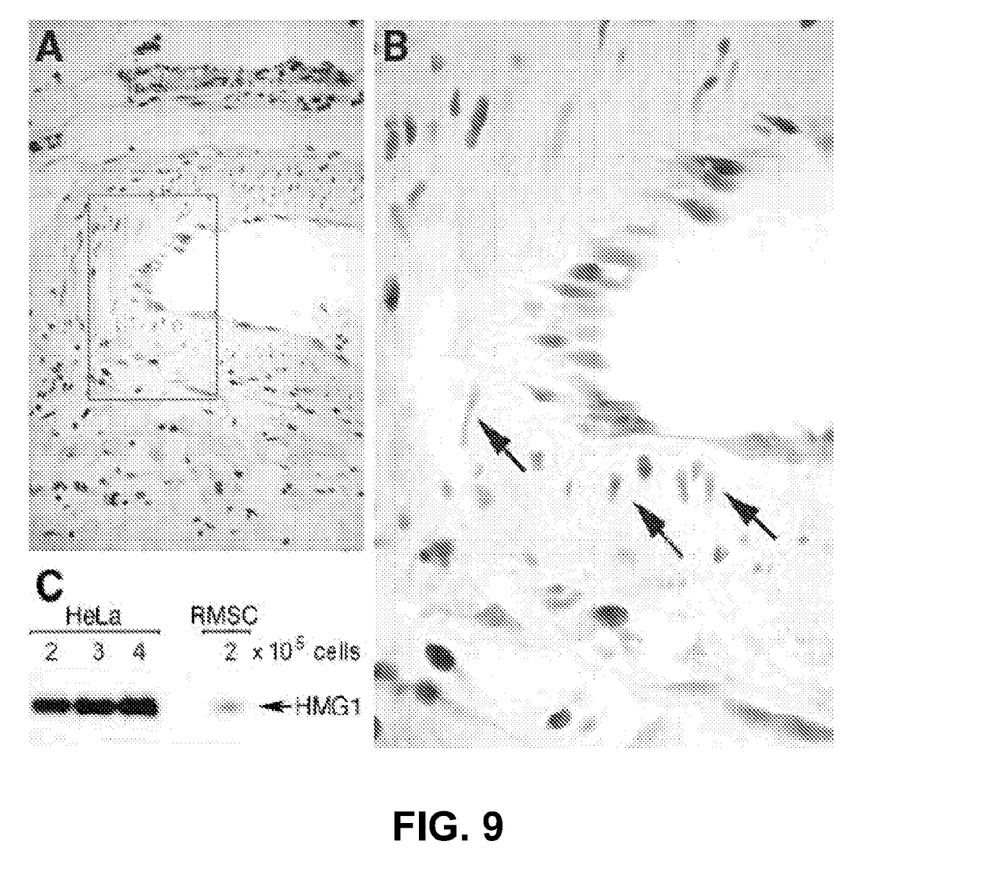
FIG. 9 shows that HMGB1 is present in the nuclei of endothelial cells, but not in those of vascular SMC.

In FIG. 9 the results of immunohistochemistry assays are shown, these data confirm that HMGB1 is contained in the nuclei of endothelial cells that line human arteries but not in the nuclei of RSMC (FIG. 9A low magnification FIG. 9-B high magnification), in fact, most nuclei of smooth muscle cells contain undetectable amounts of HMGB1 (frame in FIG. 9-B). In FIG. 9-C, Western-blot analysis shows the expression level of HMGB1 in RSMC in comparison to HeLa cells, and it demonstrates that in vitro cultures of RSMC contain low amounts of HMGB1 in comparison to HeLa cells.

Altogether, these data suggest that the HMGB1 molecules that signal to vascular smooth muscle cells may originate simply by necrosis or mechanical damages of nearby cells.

In conclusion, the above mentioned experimental data, foundations of the present invention, demonstrate that nuclear HMGB1 protein is a strong mediator of vascular remodeling occurring after mechanical damage and/or inflammation and can be passively released by damaged or necrotic cells.

In particular these data suggest what follows:

HMGB1 Act as a Chemoattractant

HMGB1 is a potent chemoattractant as bFGF or fMLP in chemotaxis assays and wounding assays, and promotes changes of cell shape and of cytoskeleton organization similar to those observed with pro-urokinase these effects are specifically due to HMGB1 and not to potential contaminants. In addition, antibodies directed against HMGB1 inhibit its effects on cell migration, whereas non specific control antibodies are unable to do so.

Binding to RAGE Initiates the HMGB1 Signaling Pathway in RSMC

The above reported experiments show that RAGE is expressed in RSMC, and anti-RAGE antibodies inhibit the effect of HMGB1 on RSMC.

It was confirmed that MAP kinases are involved in HMGB1-induced cell migration of RSMC, since ERK1/2 are phosphorylated and translocated to the cell nucleus upon HMGB1 stimulation, and the MES inhibitor PD98059 is able to block; HMGB1-induced cell migration. Data also indicate that aGi/o protein is involved in the process which is activated by HMGB1, since HMGB1-induced cell migration can be blocked by *Bordetella pertussis* toxin. G protein are usually associated to seven-transmembrane-elix receptors (7 TM), but so far no direct association between RAGE and G protein has been described. Up to now, it is unknown if HMGB1 need to bind a 7 TM receptor/G protein receptor in addition to RAGE, or if a G protein is involved downstream to RAGE, or in a feedback mechanism.

HMGB1 Paracrine Function

HMGB1 is released in a unregulated manner, which means upon stimulation with cytolcines or lipopolysaccharide, when cells are mechanically damaged or undergo necrosis. Thus, HMGB1 can signal the damage or destruction of an individual cell to the neighbouring cell in a paracrine manner. The cells that respond to extracellular HMGB1 appear to contain very little HMGB1 themselves, and almost none in the nucleus. RSMC contain very little HMGB1 compared with HeLa cells or endothelial cells, and what little HMGB1 they contain is mainly located in the cytoplasm. Migrating RSMC tend to concentrate HMGB1 on their surface at the leading edge of the cell. It can be supposed that HMGB1-responsive cells could contain little HMGB1 to reduce the chance of inappropriate responses to their own HMGB1. Concentration of HMGB1 at the leading edge of migrating cells might evoke HMGB1-induced responses in neighbouring cells relocation of molecules involved in cell migration, such as integrins, the urokinase receptor, or c-Src, is a feature of motile RSMC.

Migration also involves the activation of extracellular proteases, and the interaction between HMGB1 and the plasminogen activation system might facilitate cell migration within the extracellular matrix.

ROLE of HMGB1 in Vasculopathies

The responsiveness of smooth muscle cells to HMGB1, the observation that endothelial cells contain high amounts of HMGB1 while vascular SMC contain little, and the release of HMGB1 from cells undergoing mechanical damage, all the above results point to a possible role of HMGB1 during the tissue remodeling occurring in atherosclerosis and restenosis.

The above specified experimental results permitted to identify the molecules, object of the invention, able to inhibit the interaction between HMGB1 and RAGE receptor; these molecules are classified, considering their structural and functional characteristics, as follows:

1. HMGB1 antagonists: HMGB1 fragments, HMG box analogues, which can be more effective than the entire full-length molecule, and proteins containing HMG box domains, the last two are both able to bind to RAGE receptor.

2. HMGB1 inhibitors: molecules, as antibodies or antibody fragments and four-way DNA, which bind to HMG box domain and avoid HMGB1 binding to RAGE.

These molecules are advantageously used for pharmacological preparation which prevent, retard or minimise atherosclerosis and/or restenosis after vascular epithelium damages, including those events that occur after angioplasty.

Furthermore, the inventors of the present invention demonstrated that HMGB1 has a strong biological effect on mouse embryonic fibroblasts. It is well known that fibroblasts are the main cellular components of connective tissues and they are responsible for the synthesis and upkeeping of the connective extracellular matrix. More particularly, HMGB1 acts in vitro as a potent chemoattractant for fibroblasts and anti-RAGE antibodies block said effect.

Consequently, every kind of molecules having homology with HMGB1 can be used, as the entire fulllength protein, for the preparation of pharmacological agents which positively regulate, thus facilitate and/or induce cellular migration of fibroblasts. In the same way, every kind of molecules able to block the interaction between HMGB1 and its RAGE receptor (i. e. all the molecules belonging to the inhibitors group: antibodies or antibodies fragments, four-way DNA; and all the molecules belonging to the HMG box-antagonists group: HMGB1 fragments, molecules containing the HMG box domain) can efficiently be used for the production of pharmacological agents in order to avoid, retard or reduce connective tissues regeneration.

An additional aim of the present invention is the use of HMGB1, HMGB1 fragments corresponding to HMG box, HMG box domains of other proteins belonging to the HMG box family and other proteins of the HMG-box family, for the preparation of therapeutic agents which facilitate and/or induce fibroblasts migration and consequently positively regulate connective tissues regeneration.

It is an integral part of the present invention the use of all the molecules, antagonists and/or inhibitors, which inhibit the interaction between HMGB1 and RAGE receptor, for the preparation of therapeutic agents which reduce, retard, and avoid connective tissues regeneration, as focused by the following experiments.

Chemotaxis Assay on Fibroblasts

Chemotaxis assays were performed using well-know protocols (Degryse et al., 1999, Blood, 94:64. 9-662). Modified Boyden chambers were used with filters having 0.5 ym pore size (Corning, Acton, Mass.) and treated with collagen l (100 pg/ml in 0.5 M acetic acid) and fibronectin (10 llg/ml) (Roche). Mouse embryonic fibroblasts were cultured following well-known protocols (Calogero et al., 1999, Nat. Genet., 22: 276280) and after 24 hours of serum starvation, a sample of 20,000-40,000 cells was added to the upper well of Boyden chamber. $E.\ coli$ expressed recombinant-HMGB1 was diluted in the same serum-free medium and added to the lower well. Anti-RAGE antibodies (1000 ng/ml) (kind gift of Dr. A. M. Schimdt, Columbia University, N.Y.) were added in both wells.

Overnight cell migration was allowed at 37 C, then cells remaining on the upper surface of filters were scraped off and filters were fixed in methanol and stained in a solution of 10% crystal violet in 20% methanol. All experiments were performed at least twice in triplicate.

Figure 10:
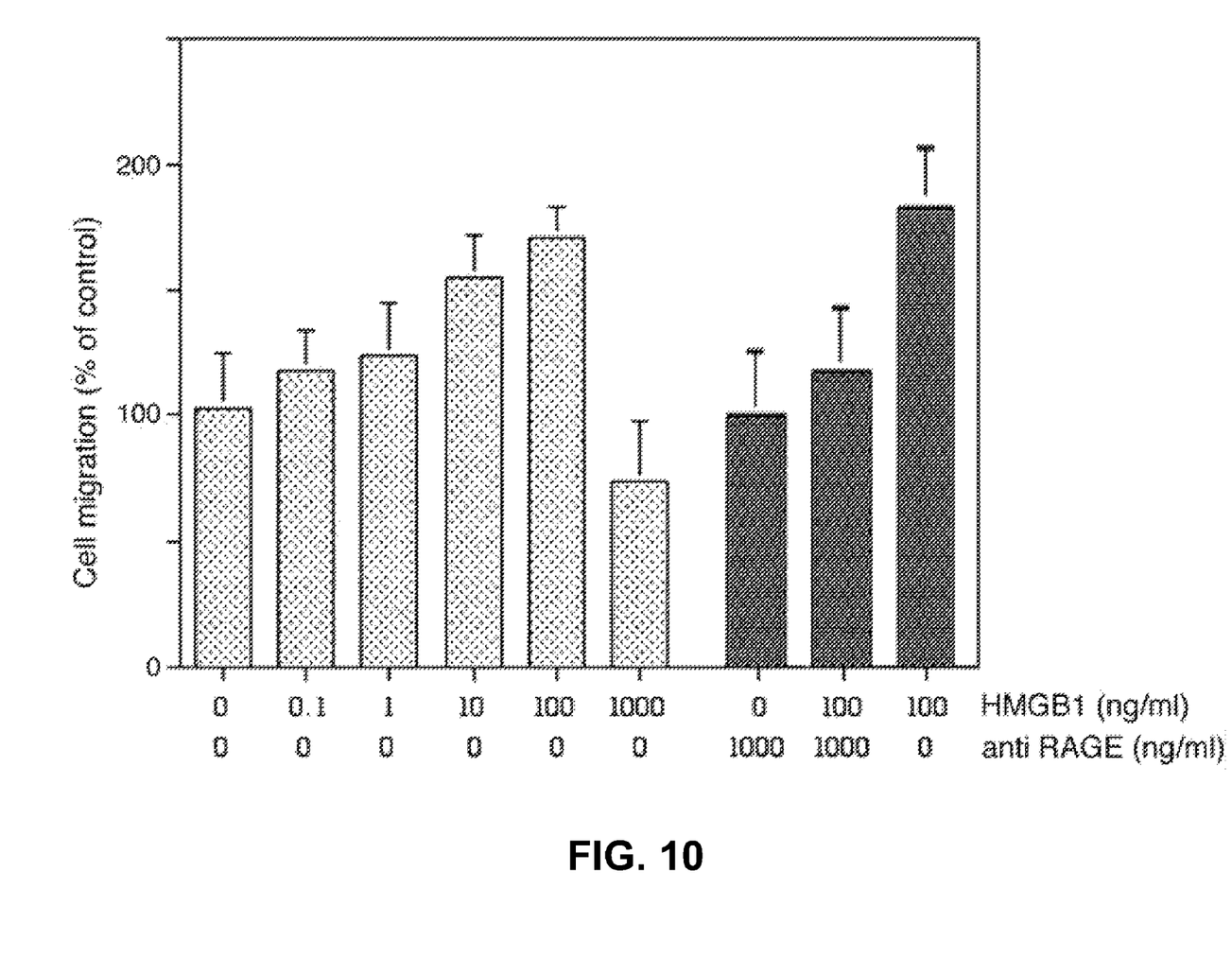
FIG. 10 shows the chemotactic effect of HMGB1 on mouse embryonic fibroblasts in chemotaxis assays performed using modified Boyden chambers, in the presence or in the absence of anti-RAGE antibodies (1000 ng/ml). The value of 100 corresponds to the number of cells migrating in the absence of any stimulator (random cell migration). The data represent the mean+SD (n=3).

Results, as shown in FIG. 10 are the mean W SD of the number of cells counted in 10 high power fields per filter and expressed as fold over untreated control. To random cell migration(i. e. migration in absence of chemoattractant) was given the arbitrary value of 100%.

Statistical analysis was performed using an ANOVA model for the evaluation of treatments with increasing doses of a reagent. $E.\ coli$ expressed recombinant-HMGB1 stimulates fibroblasts migration in a concentration-dependent manner, starting at doses as low as 0.1 ng/ml and with a maximal response at 100 ng/ml, at higher doses (1000 ng/ml) the response is lower than the control. Anti RAGE antibodies (1000 ng/ml) totally block the migratory response (right side of the graphic of FIG. 10) showing that this is specifically due to HMGB1.

Role of HMGB1 in the Regulation of Connective Tissue Regeneration

The responsiveness of fibroblasts to HMGB1 points out to a possible role of HMGB1 during connective tissues remodelling occurring after damages due to traumatic events or surgery. Moreover, the fact that anti-RAGE antibodies block said response demonstrates that the interaction between HMGB1 and RAGE receptor on cellular surface is the basic event leading to fibroblast sensitiveness to HMGB1.

In conclusion:

HMGB1 and/or HMGB1 fragments corresponding to HMG box, HMG box domains of other proteins belonging to HMG-box family and other proteins of the HMG-box family are advantageously used for pharmacological preparations which positively regulate, i.e. facilitate and/or induce e connective tissues regeneration.

every kind of molecules able to inhibit the interaction between HMGB1 and RAGE, belonging to the antagonists group, (able to bond to RAGE receptor), and belonging to the inhibitors group, (i.e. able to bound the HMG box domain blocking HMGB1 bounding to RAGE receptor) are advantageously used for pharmacological preparations which negatively regulate, i.e. block, retard or reduce connective tissues regeneration.

The invention claimed is:

1. A method of promoting connective tissue remodeling, comprising:
administering, to a subject in need thereof, a molecule selected from the group consisting of: HMGB1, an 80 amino acid HMGB1 Box A domain and an 80 amino acid HMGB1 Box B domain.

2. A method of promoting wound healing, comprising:
administering to an individual in need thereof HMGB1, an 80 amino acid HMGB1 Box A domain and an 80 amino acid HMGB1 Box B domain.

3. The method of claim 2, wherein the wound comprises connective tissue damage.

* * * * *